(12) United States Patent
Allen et al.

(10) Patent No.: US 10,949,772 B2
(45) Date of Patent: **\*Mar. 16, 2021**

(54) SYSTEM FOR EVALUATING JOURNAL ARTICLES

(71) Applicant: International Business Machines Corporation, Armonk, NY (US)

(72) Inventors: Corville O. Allen, Morrisville, NC (US); John M. Cusick, Harrison, NY (US); Shannen B. Lambdin, Morrisville, NC (US); Nicolas B. Lopez, Austin, TX (US); Anuj Sharma, Saratoga, CA (US)

(73) Assignee: International Business Machines Corporation, Armonk, NY (US)

( \* ) Notice: Subject to any disclaimer, the term of this patent is extended or adjusted under 35 U.S.C. 154(b) by 645 days.

This patent is subject to a terminal disclaimer.

(21) Appl. No.: 15/413,686

(22) Filed: Jan. 24, 2017

(65) Prior Publication Data

US 2018/0211174 A1 Jul. 26, 2018

(51) Int. Cl.
*G06N 20/00* (2019.01)
*G06F 16/35* (2019.01)
(Continued)

(52) U.S. Cl.
CPC ............. *G06N 20/00* (2019.01); *G06F 16/35* (2019.01); *G16H 20/10* (2018.01); *G16H 70/20* (2018.01); *G16H 70/40* (2018.01); *G06N 5/04* (2013.01)

(58) Field of Classification Search
CPC .......... G06N 20/00; G06N 5/04; G16H 70/40; G16H 20/10; G16H 70/20; G06F 16/35
See application file for complete search history.

(56) References Cited

U.S. PATENT DOCUMENTS 6,192,360 B1 \* 2/2001 Dumais ................ G06K 9/6269
7,529,737 B2 5/2009 Aphinyanaphongs et al.
(Continued)

FOREIGN PATENT DOCUMENTS

WO 2015017726 2/2015

OTHER PUBLICATIONS

Dave et al, "Mining the Peanut Gallery: Opinion Extraction and Semantic Classification of Product Reviews", May 2003, all pages (Year: 2003).\*

(Continued)

*Primary Examiner* — Daniel C Puentes
(74) *Attorney, Agent, or Firm* — Andrew DeLizio; Randy E. Tejeda (57) ABSTRACT

A method of machine learning that teaches a computer to determine likelihood that a medical journal article is classified as high value for an intended system. In some embodiments, the method includes procuring, in a medical articles database on the computer, a training set including medical articles recommended by subject matter experts associated with medical journals that have published the medical articles. The method can also include identifying, by a feature extraction controller of the computer, first features in the medical articles via a remote annotation service and a remote article information service. The method can also include identifying, by intended system services electronically available to the intended system, second features in the medical articles. The method can also include reducing, by the feature extraction controller, the first and second features to form a set of relevant features.

21 Claims, 8 Drawing Sheets

(51) Int. Cl.
*G16H 70/40* (2018.01)
*G16H 20/10* (2018.01)
*G16H 70/20* (2018.01)
*G06N 5/04* (2006.01)

(56) References Cited

U.S. PATENT DOCUMENTS

| | | | | |
|---|---|---|---|---|
| 2005/0086078 | A1* | 4/2005 | Maloney | G06F 19/325 705/2 |
| 2014/0147048 | A1* | 5/2014 | Yang | G06F 16/353 382/190 |
| 2014/0297297 | A1* | 10/2014 | Head | G16H 50/20 705/2 |
| 2018/0211173 | A1 | 7/2018 | Allen | |

OTHER PUBLICATIONS

Afzal et al., "Relevant Knowledge Acquisition and Appraisal using Knowledge-intensive Queries", Feb. 2016, IEEE Xplore, all pages (Year: 2016).*

Ganiz, et al., "Recent Advances in Literature Based Discovery", J of the American Society for Information Science and Technology, JASIST, 2005, 45 Pages.

Kiritchenko, et al., "ExaCT: Automatic Extraction of Clinical Trial Characteristics from Journal Publications", BMC Medical Informatics and Decision Making, 2010, 17 Pages.

Kovačević, et al., "Mining methodologies from NLP publications: a case study in automatic terminology recognition", Apr. 2012, 31 pages.

Kröll, et al., "Towards a Marketplace for the Scientific Community: Accessing Knowledge from the Computer Science Domain", D-Lib Magazine, vol. 20, No. 11/12, Dec. 2014, 9 pages.

Serenko, et al., "Comparing the expert survey and citation impact journal ranking methods: Example from the field of Artificial Intelligence", J of Informetrics 5, 2011, 20 pages.

Appendix P—List of IBM Patents or Patent Applications Treated as Related, Filed herewith, 2 Pages.

Afzal et al ("Relevant Evidence Acquisition and Appraisal using Knowledge-intensive Queries" 2016) (Year: 2016).

* cited by examiner

TITLE: A TREATMENT FOR DISEASE

ABSTRACT: THIS ARTICLE DESCRIBES A STUDY IN WHICH DRUG THERAPIES HAVE SHOW SUCCESS IS ELIMINATING SYMPTOMS FOR A DISEASE.

TEXT1 TEXT TEXT TEXT TEXT
TEXT TEXT TEXT2 TEXT TEXT
TEXT3 TEXT TEXT TEXT TEXT
TEXT TEXT TEXT TEXT TEXT4
TEXT TEXT TEXT TEXT TEXT
TEXT TEXT TEXT TEXT TEXT

TITLE: A TREATMENT FOR DISEASE

ABSTRACT: THIS ARTICLE DESCRIBES A STUDY IN WHICH DRUG THERAPIES HAVE SHOW SUCCESS IS ELIMINATING SYMPTOMS FOR A DISEASE.

*TEXT1* TEXT TEXT TEXT TEXT
TEXT TEXT *TEXT2* TEXT TEXT
*TEXT3* TEXT TEXT TEXT TEXT
TEXT TEXT TEXT TEXT *TEXT4*
TEXT TEXT TEXT TEXT TEXT
TEXT TEXT TEXT TEXT TEXT

306
FEATURES:
1. DRUG XXX
2. DRUG THERAPY
3. SYMPTOM
4. TEXT1
5. TEXT 2
6. TEXT 3
7. TEXT 4

LABLE:
HIGH VALUE ARTICLE
308

304
META DATA
FUNDING SOURCE: NATIONAL SCIENCE FOUNDATION
TYPE OF STUDY: DOUBLE BLIND STUDY
DRUGS TESTED: DRUG XXX

SYSTEM FOR EVALUATING JOURNAL ARTICLES

BACKGROUND

Embodiments of the inventive subject matter generally relate to the field of computer systems, and more particularly to computer systems that implement techniques for natural language processing and machine learning to score journal articles.

The amount of medical literature is increasing at an exponential rate. Given the volume of medical literature, it is becoming increasingly difficult to identify relevant, high-quality medical journals. Assessing the value of medical journals is becoming increasingly important to both doctors, businesses, and others. Many doctors constantly strive to identify relevant, high-quality literature to stay up-to-date on medical technologies. Some businesses seek relevant, high-quality medical literature for use in cognitive applications. These businesses need methods for assessing value of medical content. Similarly, publishing companies who aggregate medical journals and sell subscription contracts need ways to rank journals in order of most useful and profitable. Currently, there is no comprehensive system that automatically assesses the value of medical journals by evaluating factors other than citation frequency.

SUMMARY

A method of machine learning that teaches a computer to determine likelihood that a medical journal article is classified as high value for an intended system. In some embodiments, the method includes procuring, in a medical articles database on the computer, a training set including medical articles recommended by subject matter experts associated with medical journals that have published the medical articles. The method can also include identifying, by a feature extraction controller of the computer, first features in the medical articles via a remote annotation service and a remote article information service. The method can also include identifying, by intended system services electronically available to the intended system, second features in the medical articles. The method can also include reducing, by the feature extraction controller, the first and second features to form a set of relevant features. wherein the reducing is based on the first and second features of each medical article in the training set, information about the medical articles provided by the intended system services, and a classification label associated with each medical article; adapting, by a classifier of the computer, a classification function based on the relevant features of each medical article in the training set, and on the classification label of each medical article; after the adapting, selecting, by the classifier on the computer, a new medical article to classify; and determining, by the classifier on the computer, a probability that the new medical article is classified as high value.

BRIEF DESCRIPTION OF THE DRAWINGS

The present embodiments may be better understood, and numerous objects, features, and advantages made apparent to those skilled in the art by referencing the accompanying drawings.

DESCRIPTION OF EMBODIMENT(S)

The description that follows includes exemplary systems, methods, techniques, instruction sequences and computer program products that embody techniques of the present inventive subject matter. However, it is understood that the described embodiments may be practiced without these specific details.

Introduction to Some Embodiments

Some embodiments of the inventive subject matter can determine a score for medical journal articles, where the score indicates a probability that an article is of high quality. Some embodiments use natural language processing and machine learning to train a classifier to determine such a score for the medical journal articles. In addition to analyzing articles, some embodiments can indicate whether entire medical journals are high-quality. Doctors, business professionals, and others can use the scores to determine value for particular medical journals. Doctors may use these scores in searching for high-value journals to stay abreast of new technologies. Business professionals may use the scores to determine monetary value for journal articles. Although this document refers to "medical journal articles", the articles discussed herein can relate to any subject matter (e.g., law journal articles, physics journal articles, etc).

Figure 1:
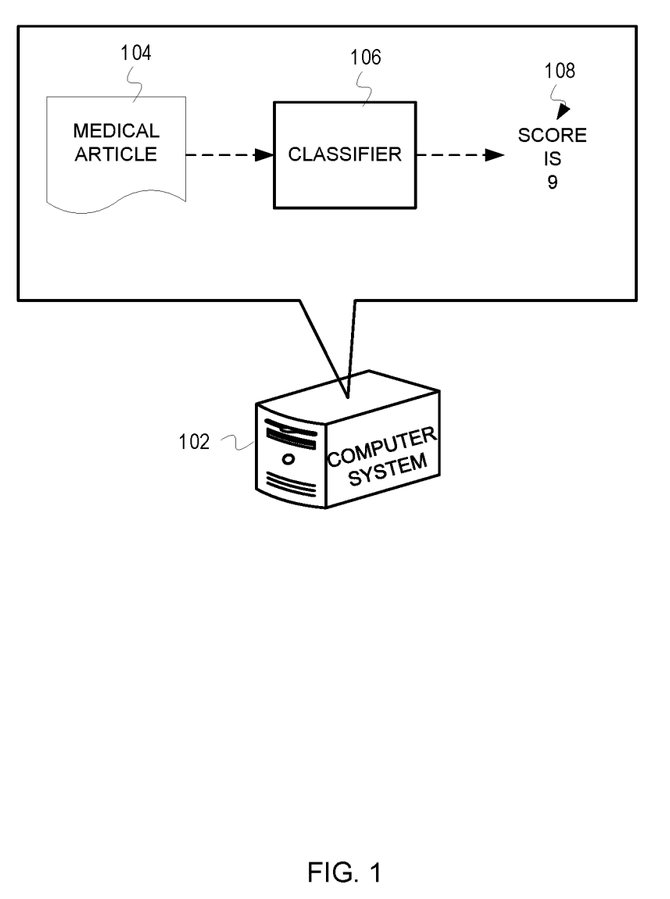
FIG. 1 is a block diagram showing a computer system capable of scoring medical journal articles and medical journals, according to some embodiments of the inventive subject matter.

FIG. 1 is a block diagram showing a computer system capable of scoring medical journal articles and medical journals, according to some embodiments of the inventive subject matter. As shown, a computer system 102 includes a classifier 106. The classifier 106 is configured to process medical journal articles 104, and provide scores indicating a probability that those medical journal articles are high-quality. For example, the score may range from 0-10, where 10 is the highest probability. As shown, the classifier determines a score of "9" for the medical article 104. Such a score indicates a relatively high probability that the medical article 104 is high-quality.

The medical articles may be in text form, and may be received (over an electronic network) from various remote electronic repositories. Before the classifier 106 processes the articles, remote services (not shown in FIG. 1) may process the articles to provide annotations and natural language data. Other components of the computer system 102 (not shown) may use the annotations and natural language data to determine features for the medical articles 104.

Before processing the articles, the classifier 106 may perform a machine learning process based on a training set of articles. The training set may include articles labeled as high-quality and articles labeled as low-quality, where each label may indicate a classification for an article. The classifier 106 uses the training set to determine a function for assigning scores to new articles. After the machine learning process, the classifier 106 is configured to provide scores that indicate a probability of whether a medical journal article is high-quality.

More About Some Embodiments

The following discussion will first describe example components included in some embodiments, and then describe example operations performed by some embodiments.

Figure 2:
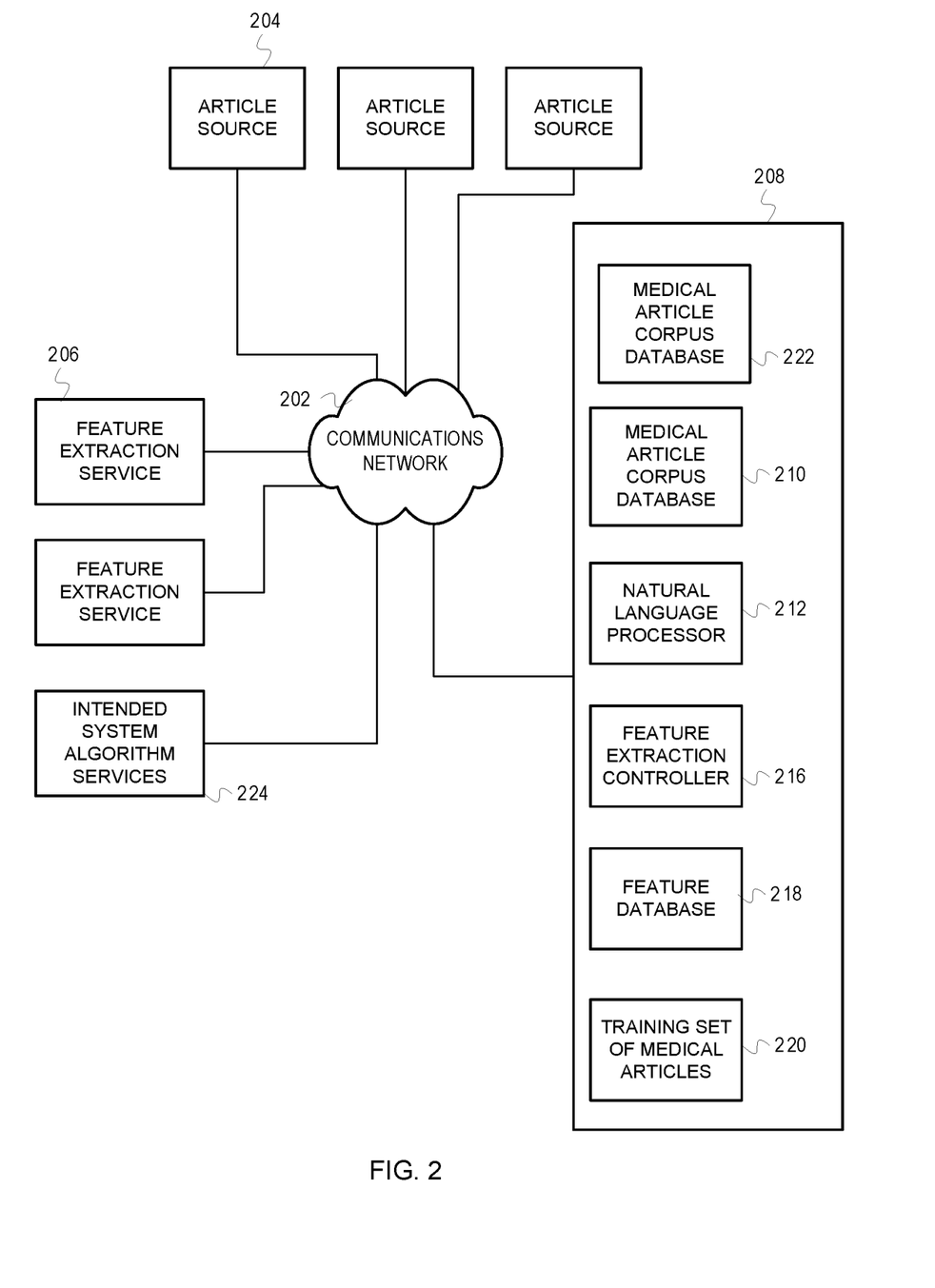
FIG. 2 is a block diagram illustrating a system for scoring medical journal articles, according to some embodiments of the inventive subject matter.

FIG. 2 is a block diagram illustrating a system for scoring medical journal articles, according to some embodiments of the inventive subject matter. In FIG. 2, the system 200 includes a communication network 202 connected to a scoring computer 208, article information service 206, intended system service 226, annotation service 224, and article sources 204. As shown, the scoring computer 208 includes a classifier 222, medical article corpus database 210, natural language processor 212, feature extraction controller 216, feature database 218, and training set of medical articles 220.

Figure 3A:
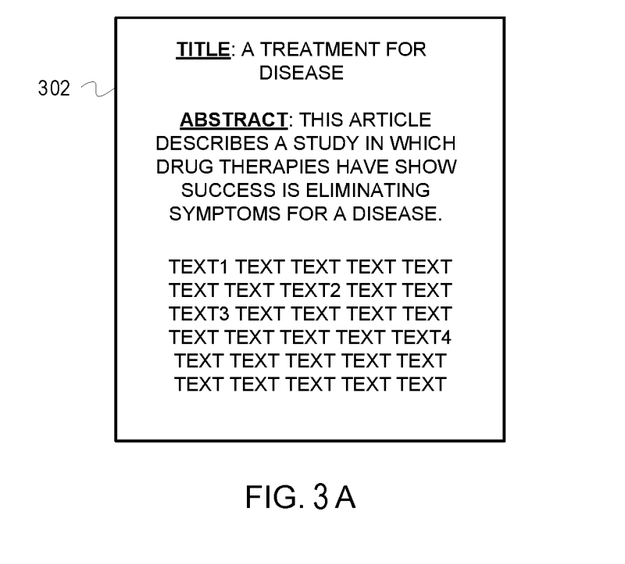
FIG. 3A is a block diagram illustrating an example electronic article, according to some embodiments.

During operation, the scoring computer 208 receives articles into the medical articles corpus database 210 from one or more article sources 204. The article sources 204 can be any suitable online repositories for medical journal articles, such as F1000.com, JWatch.org, etc. The medical journal articles can be from any published medical journal, such as the New England Journal of Medicine, Journal of the American Medical Association, etc. FIG. 3A is a block diagram illustrating an example electronic article, according to some embodiments. As shown, in FIG. 3A, the article 302 includes a title, abstract, and main body of text 304. The article 302 may include other text or graphical information, such as tables of contents, bibliography, tables, charts, drawings, etc.

After receiving a corpus of articles in the medical article corpus database 210, the scoring computer 208 prepares the articles for a machine learning process to be controlled by the classifier 222. To prepare the articles, the feature extraction controller 216 determines features for the articles in the database 210. Features are article characteristics that support a particular score. The scoring computer's classifier 222 will examine an article's features to determine the article's score (described in more detail below).

As part of determining features for the articles in the database 210, the feature extraction controller 216 utilizes the annotation service 224. The annotation service 224 executes, for each article in the database 210, pre-defined bio-medical name entity recognizers to identify entity types, such as disease types (e.g., cancer types), patient characteristics, drug types, etc. In some embodiments, there are over 300 entity types recognized by the annotation service 224. The feature extraction controller 216 may mark the article to indicate these entities or otherwise store information indicating the entities associated with an article (e.g., in the feature database 218). Additionally, the feature extraction controller 216 may also indicate a frequency of each entity type in an article.

After determining entities, feature extraction controller 216 can utilize the article information service 206 to determine more information (e.g., features) about each article. In one embodiment, the article information service 206 is PubMed (www.pubmed.gov), which provides four categories of data: publication type, substance type, grant type, and MeSH (Medical Subject Headings) terms. Each article can have one or more terms in each category of data. Publication types will indicate what type of article was published (e.g. meta-analysis, cohort study, review). Substance types will indicate the types of drugs mentioned in a study. Grant types will include any funding sources of a study (e.g. NIH). MeSH terms (Medical Subject Heading Terms) take on a variety of different values, including terms related to patient characteristics (e.g. female, over age 80), and experimental procedures (e.g. double blinding). Each article may have approximately 20 MeSH terms. The feature extraction controller 216 may mark the article to indicate these terms or otherwise store information indicating the entities associated with an article. The article information service 206 can be any suitable service that provides information about an article, such as information that is not available in the article's text.

The feature extraction controller 216 may also call the natural language processor 212 to process the articles. In some embodiments, the natural language processor 212 identifies unigrams and bigrams in each article's text, abstract, and title. At this point, the feature extraction controller 216 may have identified for each article numerous entities, terms, and natural language data—all of which constitute features for each article. In some embodiments, an article's features are stored in association with the article. Alternatively, the article may be marked to indicate the features. The feature extraction controller 216 can store a dictionary of these features in the feature database 218.

Figure 3B:
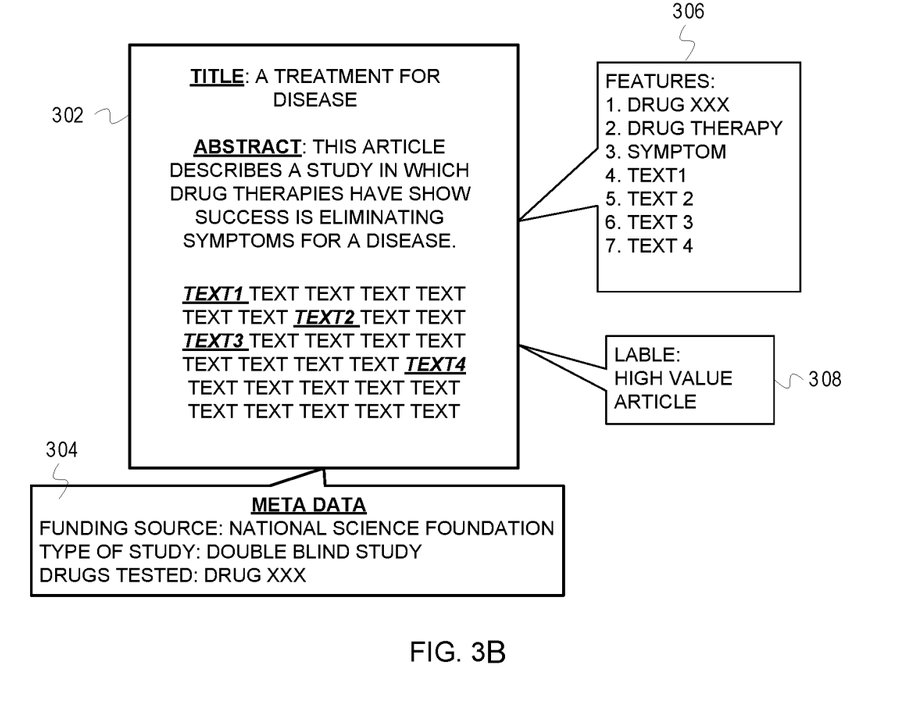
FIG. 3B is a block diagram showing information that may be associated with articles in the database, according to some embodiments.

After identifying features in the articles, the scoring computer 208 undertakes a machine learning process. To facilitate the machine learning process, the scoring computer 208 determines a training set of medical articles 220. The training set includes articles that are labeled to indicate whether they are high-quality. Additionally, as noted above, articles in the training set have been through a process that identifies features in the articles. FIG. 3B is a block diagram showing information that may be associated with articles in the database, according to some embodiments. FIG. 3B shows the article 302 along with a label 308. In some embodiments, the scoring computer 208 receives data input indicating labels for articles of the database 210. As shown, the label 308 indicates that the article 302 is a high-quality article. During the training process, the classifier 222 processes articles in the training set to determine a function that produces a score for new articles. The classifier 222 uses each article's label 308 and features 306 in determining the function. After completing the machine learning process, the classifier 222 can provide a score for a new medical article, where the score indicates a probability that the article is high-quality. Additionally, the classifier 222 can process articles and provide scores indicating probability of an entire journal being high-quality.

The components shown in FIG. 2 can be subdivided or integrated in any suitable fashion. Furthermore, the components can be local or remote. Additionally, the components can include circuitry, machine-readable storage media storing program code, or any other suitable means for implementing the functionality described herein.

Figure 4:
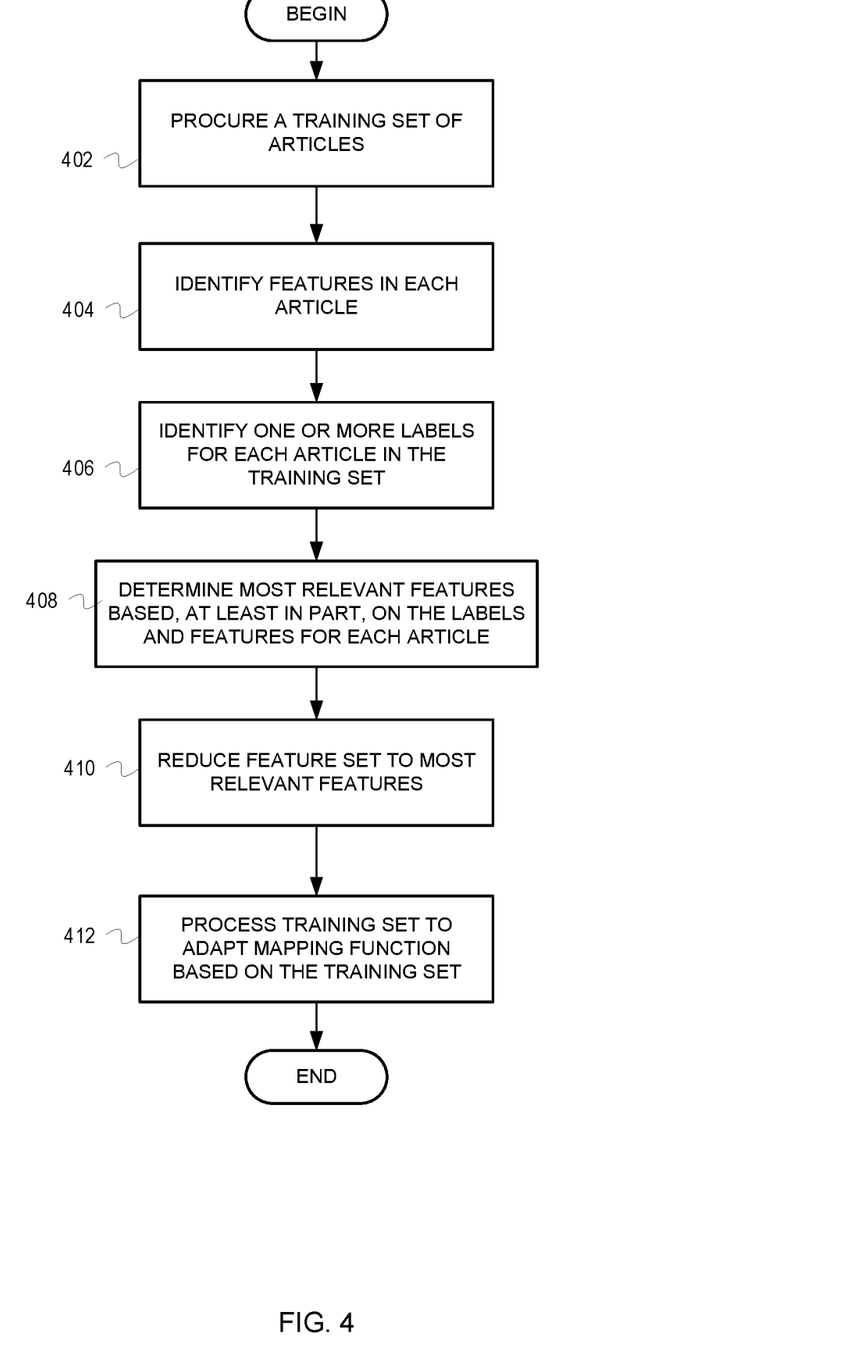
FIG. 4 is a flow diagram illustrating operations for a machine learning process, according to some embodiments of the inventive subject matter.

This discussion will continue with a description of operations performed by some embodiments of the inventive subject matter. The following discussion describes embodiments in which operations shown in FIGS. 3 and 4 are performed components shown in FIG. 2. However, in some embodiments, the operations may be performed by different components, including components not shown herein.

FIG. 4 is a flow diagram illustrating operations for a machine learning process, according to some embodiments of the inventive subject matter. In FIG. 4, the flow 400 begins at block 402, where a scoring computer 208 identifies a training set of articles. In some embodiments, the scoring computer 208 procures high-quality articles from medical journals that include articles recommended by subject matter experts. In some embodiments, the high-quality articles are randomly selected from those recommended by the subject matter experts. In some instances, the scoring computer 208 receives input (e.g., from an operator) identifying such sources (e.g., Journal Watch, F1000.com, etc.). In turn, the training computer 208 electronically receives the articles from the article sources 204 over a communications network 202. In one embodiment, 10,000 articles from such sources will be labeled as high-quality articles (see block 406). In one embodiment, for each high-quality article published by a source, the training set includes two articles randomly selected from the same source, where the randomly selected articles were not recommended by the source's subject matter experts. Therefore, in some embodiments, the scoring computer 208 compiles a training set including 10,000 high-quality articles and 20,000 lower-quality articles. However, in some embodiments the training set can include different numbers of high and lower quality articles procured from different sources. In some embodiments, the training set is stored in the medical article database. The flow continues at block 404.

At block 404, the feature extraction controller 216 identifies features in each article of the medical article database 210 (including the training set of articles). As described above, embodiments can utilize remote article information services (see 206), remote annotation services (see 224), natural language processing (see 212), and other components for identifying features in articles. FIG. 3B shows an example article for which features have been identified (see 306). The flow continues at block 406.

At block 406, the feature extraction controller 216 identifies labels for each article in the training set. As noted above, an article's label indicates a classification for the article. For example, as shown in FIG. 3B, the label 308 indicates that the article 302 is classified as high-quality. As noted above, some embodiments procure articles that have been recommended by subject matter experts associated with the article source (e.g., subject matter experts associated a journal). For such embodiments, the scoring computer 208 labels recommended articles as "high-quality". Moreover, the scoring computer 208 labels non-recommended articles as "low-quality", or it labels them with other classifications different from "high-quality". In some embodiments, the feature extraction controller 216 receives labels as input from an operator of the scoring computer. The flow continues at block 408.

At block 408, the feature extraction controller 216 determines the most relevant features based, at least in part, on the labels and features of each article in the training set. The flow continues at block 410, where the feature extraction controller 216 employs a statistical algorithm (e.g., a chi-squared algorithm) to reduce the feature set identified at block 404 to a more relevant feature set based on features associated with articles known to be high-quality. In some embodiments, the relevant feature set is represented in the feature database 218. Some embodiments do not reduce the feature set, so they do not perform operations shown in blocks 408 and 408. The flow continues at block 412.

At block 412, the classifier 222 processes the training set to adapt a classification function based on the training set. In some embodiments, the classifier evaluates features associated with articles in the training set (e.g., recommended high-quality articles and randomly selected lower-quality articles that were note recommended) to create a classification function that classifies new articles. The classification function can be based on any suitable statistical algorithm (e.g., a regression algorithm) that classifies new articles and provides a probability that the article is high-quality. Alternatively, the classification function can be based on any suitable decision trees, support vector machines, or any other suitable supervised learning technique. After block 412, the classifier 222 is ready to score new journal articles from the database of medical journal articles. From block 412, the flow ends.

Figure 5:
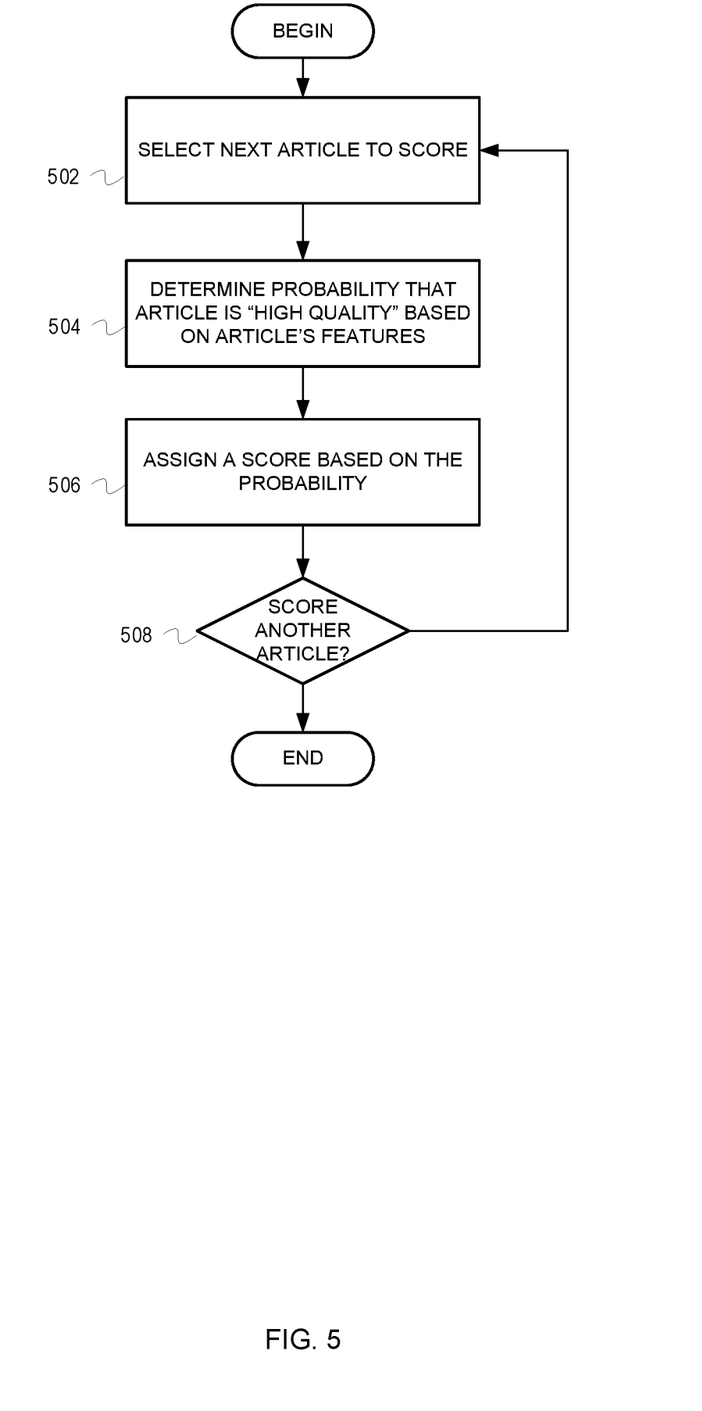
FIG. 5 is a flow diagram illustrating operations for scoring articles, according to some embodiments of the inventive subject matter.

FIG. 5 is a flow diagram illustrating operations for scoring articles, according to some embodiments of the inventive subject matter. In FIG. 5, the flow 500 begins at block 502, where a classifier 222 selects a new article to score. In some embodiments, the classifier selects an article from the medical article database 210. Flow continues at block 504.

At block 504, the classifier 222 determines a probability that the new article is high-quality. To determine the probability, the classifier evaluates the article's features, and determines a probability based on the classifier's classification function. In some embodiments, the probability is a value between 0 and 1. The flow continues at block 506.

At block 506, the classifier 222 assigned a score based on the probability. In some embodiments, the score is a value between 0-10. Hence, some embodiments multiply the probability value by 10 to achieve a score for the article. From block 506, the flow ends.

In some embodiments the classifier 222 can determine a journal level score by taking a mean of the scores for articles from a given journal. Journals can be compared and ranked based on the scores.

Additional Embodiments

The following discussion describes additional components and functionality included in some embodiments.

The discussion of FIG. 2 (above) explains how the feature extraction controller 216 can determine features related to journal articles. In some embodiments, the feature extraction controller 216 (see FIG. 2) may call intended system services 226 to determine additional features. The intended system services 226 include one or more services configured to provide features relevant to an intended system's purpose. For example, the purpose of an intended system may be to provide treatment recommendations to patients.

Figure 6:
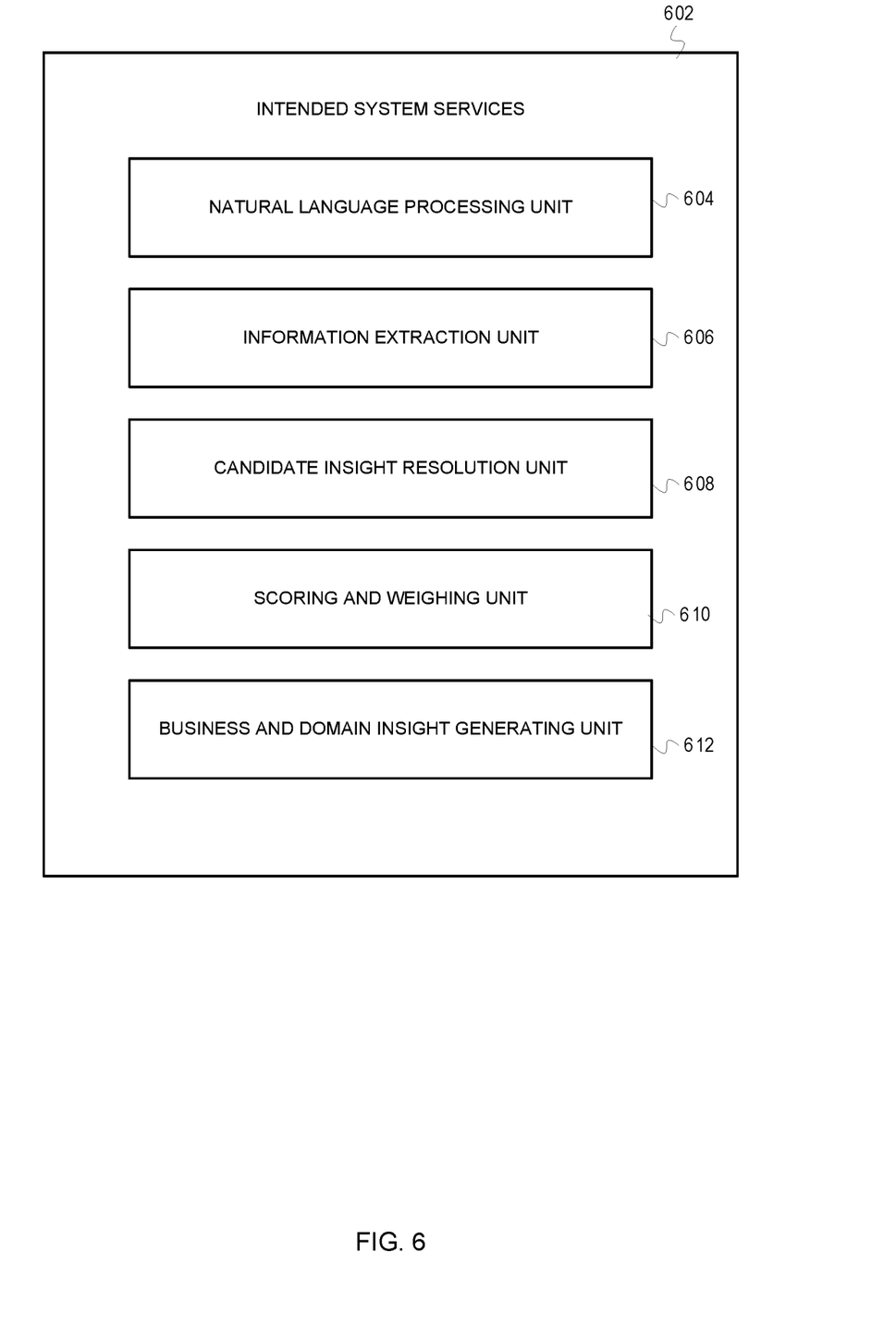
FIG. 6 is a block diagram showing components of intended system services, according to some embodiments.

FIG. 6 is a block diagram showing components of intended system services, according to some embodiments. In FIG. 6, intended system services 602 includes an information extraction unit 606, natural language processing unit 604, scoring and weighting unit 610, and business domain insight generating unit 612. The natural language processing unit 604 can include natural language processing capabilities particular to an intended system's purpose, such as such as processing natural language in ways effective in identifying information useful in recommending treatment for patients. The components of the intended system services 602 can use the natural language processing unit 604 to process natural language in articles and documents.

The information extraction unit 606 can identify annotations and insights in articles and documents. Insights may constitute aggregations of features identified in the articles and documents. The entire set of insights may be referred to as the "candidate insights." The intended system services 602 may utilize the scoring and weighting unit 610 to reduce the candidate insights into a more relevant insight list (i.e., a more relevant feature list). The scoring and weighting unit 610 can score and weight candidate insights based on knowledge about a problem to be solved. For example, consider the problem of finding a treatment recommendation for a particular patient, where the candidate insights include a long list of possible treatments. The scoring and weighting unit 610 may have information indicating that the particular patient has allergies to certain medicines, and that the patient has already tried certain treatments. There may be many possible treatment recommendations, but the candidate insight resolution unit 608 can utilize the scoring and weighting unit 610 to score/weight possible treatment options based on knowledge of the patent's allergies, earlier treatments, etc. As a result, the scoring and weighing unit 610 can reduce the candidate insights based on knowledge about a problem to be solved. The business and domain insight generator 612 provides a resulting insights to entities that call the intended system services 602.

Figure 7:
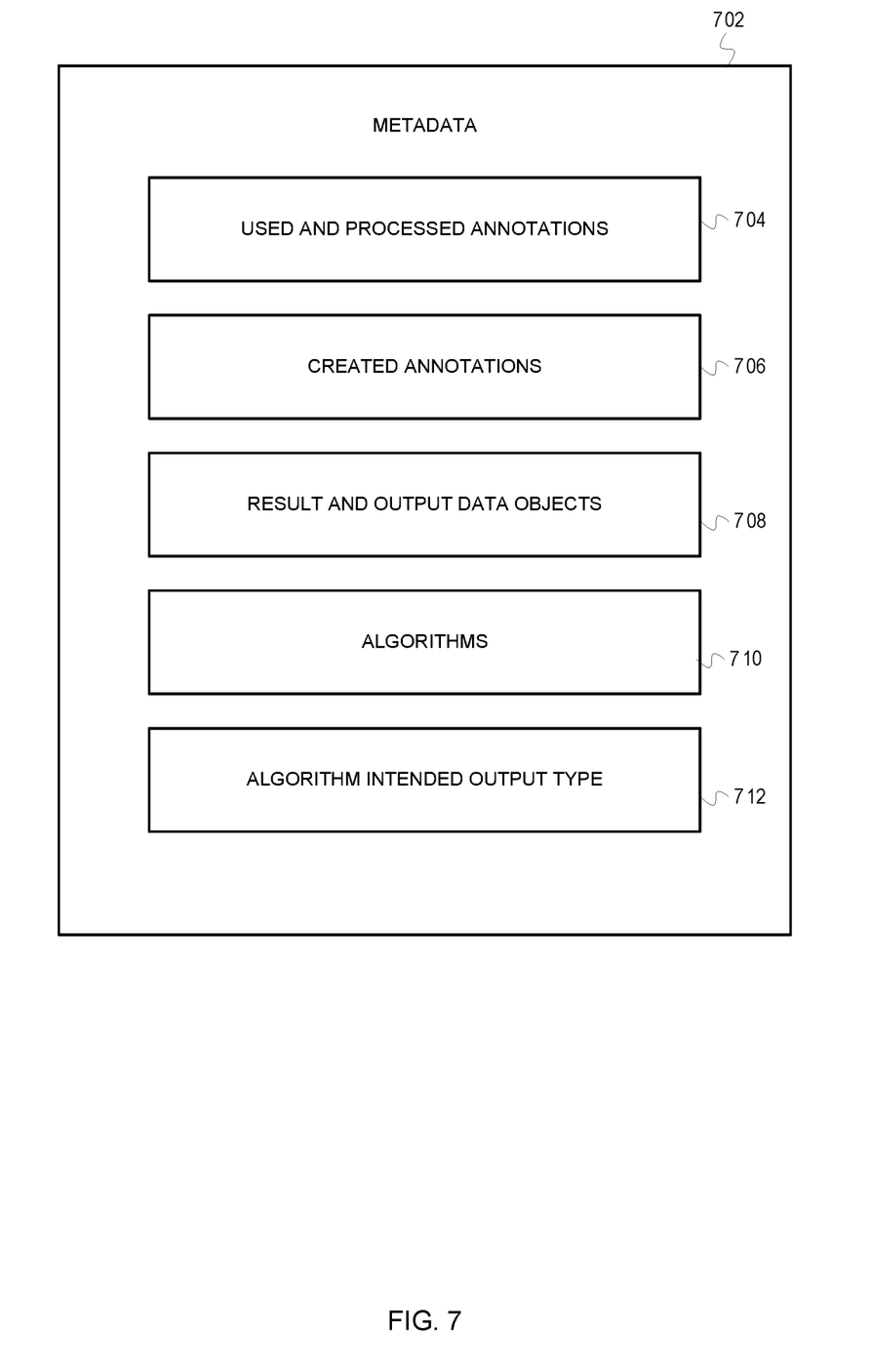
FIG. 7 is a block diagram illustrating metadata created and used according to some embodiments.

FIG. 7 is a block diagram illustrating metadata created and used according to some embodiments. In some embodiments, components of the intended system services 602 (see FIG. 6) create and use metadata shown in FIG. 7. In FIG. 7, the metadata 702 includes used and processed annotations 704, created annotations 706, result and output data objects 708, algorithms 710, and algorithm intended output type 712. The created annotations 706 can include annotations associated with articles and documents, where the annotations can include information provided by human operators. The used and processed annotations 704 can include annotations information related to annotations processed by components of the intended system services 602, such as candidate insights and extracted insights (e.g., past therapy, past treated site found in the documents or otherwise generated, etc.). The result and output data objects 708 include insights, annotations, features, and other data created by components of the intended system services 602.

The algorithms 710 include computer program code and data for facilitating functionality of some components of the intended system services 602. The algorithm intended output type 712 includes information or metadata about what type of output the components shown in FIG. 6 should produce (e.g., previous therapy, recommended therapy, etc.).

The components shown in FIGS. 6 and 7 can participate in the operations described above in the discussion of FIGS. 4 and 5. For example, the intended system services 602 can perform some or all operations of FIG. 4. As part of feature identification (see block 404), the intended system services' components can process annotations in articles, identify candidate insights in articles, use scoring and weighting algorithms to reduce candidate insights to a more relevant insight list, and use the insights to identify features for articles. In some embodiments, the intended system services 602 may utilize the scoring and weighting unit 610 to determine most relevant features based on knowledge about a problem to be solved (e.g., see block 408).

As will be appreciated by one skilled in the art, aspects of the present inventive subject matter may be embodied as a system, method or computer program product. Accordingly, aspects of the present inventive subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present inventive subject matter may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer program code for carrying out operations (e.g., operations described with respect to the flow diagrams) for aspects of the present inventive subject matter may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present inventive subject matter are described with reference to flowchart illustrations and/or block diagrams of methods, apparatus (systems) and computer program products according to embodiments of the inventive subject matter. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 8:
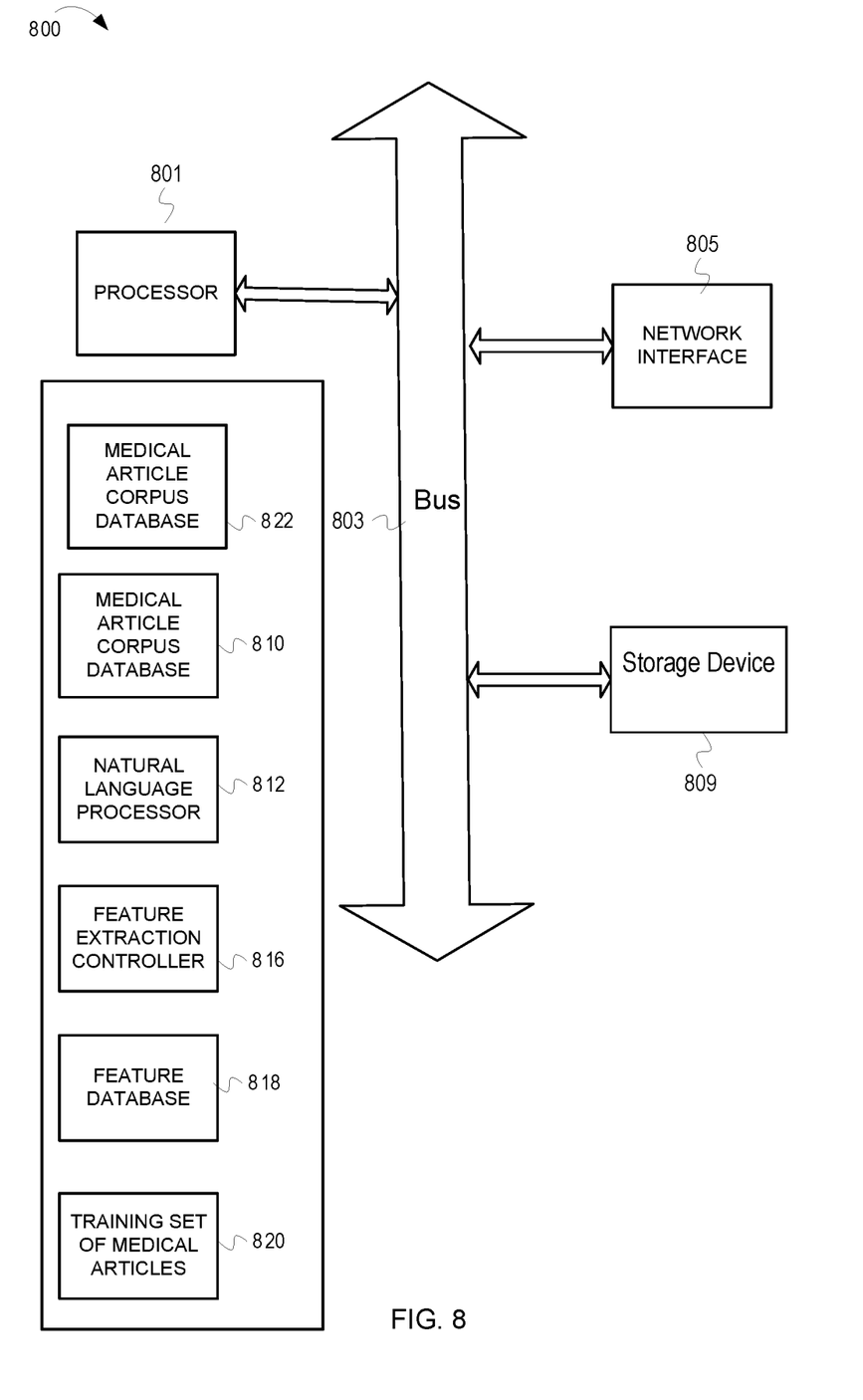
FIG. 8 depicts an example computer system.

FIG. 8 depicts an example computer system. As shown, the computer system 800 includes a processor unit 801 (possibly including multiple processors, multiple cores, multiple nodes, and/or implementing multi-threading, etc.). The computer system includes memory 807. The memory 807 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 803 (e.g., PCI, ISA, PCI-Express, HyperTransport®, InfiniBand®, NuBus, etc.), a network interface 805 (e.g., an ATM interface, an Ethernet interface, a Frame Relay interface, SONET interface, wireless interface, etc.), and a storage device(s) 809 (e.g., optical storage, magnetic storage, etc.). The system memory 807 includes components to implement embodiments described above. The system memory 807 a classifier 822, medical article corpus database 810, natural language processor 812, feature extraction controller 816, feature database 818, and training set of medical articles 820 Any one of these components may be partially (or entirely) implemented in hardware and/or on the processing unit 801. For example, the functionality may be implemented with an application specific integrated circuit, in logic implemented in the processing unit 801, in a co-processor on a peripheral device or card, etc. Further, realizations may include fewer or additional components not illustrated in FIG. 8 (e.g., video cards, audio cards, additional network interfaces, peripheral devices, etc.). The processor unit 801, the storage device(s) 809, and the network interface 805 are coupled to the bus 803. Although illustrated as being coupled to the bus 803, the memory 807 may be coupled to the processor unit 801.

While the embodiments are described with reference to various implementations and exploitations, it will be understood that these embodiments are illustrative and that the scope of the inventive subject matter is not limited to them. In general, techniques for scoring journal articles as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the inventive subject matter. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A method for determining, by a computer, likelihood that a medical journal article is classified as high value relative to other medical journal articles, the method comprising:

procuring, into a medical articles database on the computer, a training set including medical articles recommended by subject matter experts associated with medical journals that have published the medical articles, wherein each recommended medical article is associated with two randomly selected articles associated with a source of the corresponding recommended medical article;

identifying, by a natural language processor, n-grams corresponding to entities, terms, and natural language data in titles, abstracts, and text of the medical articles associated with a list of possible treatments for a patient, wherein the n-grams include disease types, patient characteristics, and drug types and corresponding frequencies in the titles, abstracts, and text of the medical articles associated with the list of possible treatments for the patient;

identifying, by a feature extraction controller of the computer, initial features in the medical articles based on the entities, terms, and natural language data;

reducing, by the feature extraction controller, the initial features to form a set of relevant features based at least in part on a classification label associated with each article utilizing a chi-squared algorithm, wherein the classification label indicates a value relative to the other medical articles;

adapting, by a classifier of the computer, a classification function based on the relevant features of the medical articles in the training set and on the classification label of each medical article utilizing supervised learning;

weighing, by a weight unit, each treatment in the list of possible treatments based on the adapted classification function, procured medical articles, patient allergies, and previously tried treatments; and recommending, by an insight resolution unit, a treatment based on the weighted list of possible treatments;

providing, by a business and domain insight generator, the recommended treatment to one or more entities, wherein the provided recommended treatment includes include annotations information, wherein annotations information constitutes aggregations of the set of relevant features.

2. The method of claim 1 further comprising:
after the adapting,
selecting, by the classifier on the computer, a new medical article to classify; and
determining, by the classifier on the computer, a probability that the new medical article is classified as high value.

3. The method of claim 1 further comprising:
assigning a score to the new medical article based on the probability.

4. The method of claim 1, the training set further includes medical articles published in the medical journals but not recommended by the subject matter experts.

5. The method of claim 1, wherein the classification labels associated with the medical articles recommended by subject matter experts indicate a classification of high quality.

6. The method of claim 1, wherein the procuring includes receiving the medical articles of the training set over a network from one or more remote computers.

7. The method of claim 1, further comprising:
a remote annotation service processing each medical article in the training set to determine pre-defined bio-medical name entities.

8. A computer program product for determining likelihood that a medical journal article is classified as high value, the computer program product comprising a computer readable storage medium having instructions executable by one or more processors to cause a computer system to:
procure, in a medical articles database on the computer system, a training set including medical articles recommended by subject matter experts associated with medical journals that have published the medical articles, wherein each recommended medical article is associated with two randomly selected articles associated with a source of the corresponding recommended medical article;

identify, by a natural language processor, n-grams corresponding to entities, terms, and natural language data in titles, abstracts, and text of the medical articles, wherein the n-grams include disease types, patient characteristics, and drug types and corresponding frequencies in the titles, abstracts, and text of the medical articles associated with the list of possible treatments for the patient;

identify, by a feature extraction controller of the computer, first features in the medical articles via a remote annotation service and a remote article information service, wherein the identification of the first features is based on the entities, terms, and natural language data;

reduce, by the feature extraction controller, the first features to form a set of relevant features based on a classification label associated with each medical article utilizing a chi-squared algorithm, wherein the classification label indicates a value relative to the other medical articles;

adapt, by a classifier of the computer system, a classification function based on the relevant features of the medical articles in the training set and on the classification label of each medical article utilizing supervised learning;

weigh, by a weight unit, each treatment in the list of possible treatments based on the adapted classification function, procured medical articles, patient allergies, and previously tried treatments; and recommend, by an insight resolution unit, a treatment based on the weighted list of possible treatments;

provide, by a business and domain insight generator, the recommended treatment to one or more entities, wherein the provided recommended treatment includes include annotations information, wherein annotations information constitutes aggregations of the set of relevant features.

9. The computer program product of claim 8, after the adaptation, select, by the classifier, a new medical article to classify; and
determine, by the classifier, a probability that the new medical article is classified as high value.

10. The computer program product of claim 9, the instructions that further cause the computer system to:
assign a score to the new medical article based on the probability.

11. The computer program product of claim 8, wherein the training set further includes medical articles published in the medical journals but not recommended by the subject matter experts.

12. The computer program product of claim 8, wherein the classification labels associated with the medical articles recommended by subject matter experts indicate a classification of high quality.

13. The computer program product of claim 8, wherein the remote annotation service is configured to process each medical article in the training set to determine pre-defined bio-medical name entities.

14. The program product of claim 8, wherein the procurement includes receipt of the medical articles of the training set over a network from one or more remote computers.

15. An apparatus comprising:
one or more processors;
a computer program product comprising a computer readable storage medium having instructions to determine likelihood that a medical journal article is classified as high value, the instructions executable by the one or more processors to cause the one or more processors to:
procure, in a medical articles database, a training set including medical articles recommended by subject matter experts associated with medical journals that have published the medical articles, wherein each recommended medical article is associated with two randomly selected articles associated with a source of the corresponding recommended medical article;
identify, by a natural language processor, n-grams corresponding to entities, terms, and natural language data in titles, abstracts, and text of the medical articles, wherein the n-grams include disease types, patient characteristics, and drug types and corresponding frequencies in the titles, abstracts, and text of the medical articles associated with the list of possible treatments for the patient;
identify, by a feature extraction controller, first features in the medical articles via a remote annotation service and a remote article information service wherein the identification of the first features is based on the entities, terms, and natural language data;
reduce, by the feature extraction controller, the first features to form a set of relevant features based on a classification label associated with each medical article utilizing a chi-squared algorithm, wherein the classification label indicates a value relative to the other medical articles;
adapt, by a classifier, a classification function based on the relevant features of the medical articles in the training set, and on the classification label of each medical article utilizing supervised learning;
weigh, by a weight unit, each treatment in the list of possible treatments based on the adapted classification function, procured medical articles, patient allergies, and previously tried treatments; and
recommend, by an insight resolution unit, a treatment based on the weighted list of possible treatments;
provide, by a business and domain insight generator, the recommended treatment to one or more entities, wherein the provided recommended treatment includes include annotations information, wherein annotations information constitutes aggregations of the set of relevant features.

16. The apparatus of claim 15, the instructions to further cause the one or more processors to:
after the adaptation,
select, by the classifier, a new medical article to classify; and
determine, by the classifier, a probability that the new medical article is classified as high value.

17. The apparatus of claim 16, the instructions to further cause the one or more processors to:
assign a score to the new medical article based on the probability.

18. The apparatus of claim 15, wherein the training set further includes medical articles published in the medical journals but not recommended by the subject matter experts.

19. The apparatus of claim 15, wherein the classification labels associated with the medical articles recommended by subject matter experts indicate a classification of high quality.

20. The apparatus of claim 15, wherein the remote annotation service is configured to process each medical article in the training set to determine pre-defined bio-medical name entities.

21. The apparatus of claim 15, wherein the procurement includes receipt of the medical articles of the training set over a network from one or more remote computers.

* * * * *